(12) United States Patent
Elmaleh et al.

(10) Patent No.: US 9,861,608 B2
(45) Date of Patent: Jan. 9, 2018

(54) METHODS FOR DELIVERING CROMOLYN

(71) Applicant: AZTHERAPIES, INC, Boston, MA (US)

(72) Inventors: David R. Elmaleh, Newton, MA (US); Alex Franzusoff, Los Altos, CA (US)

(73) Assignee: AZTHERAPIES, INC, Boston, MA (US)

( * ) Notice: Subject to any disclaimer, the term of this patent is extended or adjusted under 35 U.S.C. 154(b) by 0 days.

(21) Appl. No.: 14/893,487

(22) PCT Filed: May 22, 2014

(86) PCT No.: PCT/US2014/039118
§ 371 (c)(1),
(2) Date: Nov. 23, 2015

(87) PCT Pub. No.: WO2015/002703
PCT Pub. Date: Jan. 8, 2015

(65) Prior Publication Data
US 2016/0106704 A1  Apr. 21, 2016

Related U.S. Application Data

(60) Provisional application No. 61/826,798, filed on May 23, 2013.

(51) Int. Cl.
| | |
|---|---|
| A61K 31/352 | (2006.01) |
| A61K 9/14 | (2006.01) |
| A61K 9/00 | (2006.01) |
| A61K 31/192 | (2006.01) |
| A61K 45/06 | (2006.01) |

(52) U.S. Cl.
CPC .......... *A61K 31/352* (2013.01); *A61K 9/0075* (2013.01); *A61K 9/145* (2013.01); *A61K 31/192* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 5,655,523 | A * | 8/1997 | Hodson | A61M 15/0028 128/203.12 |
| 6,309,523 | B1 | 10/2001 | Prasnikar et al. | |
| 6,309,623 | B1 * | 10/2001 | Weers | A61K 9/0073 424/45 |
| 2004/0223918 | A1 | 11/2004 | Pham et al. | |
| 2006/0159629 | A1 | 7/2006 | Tarara et al. | |
| 2007/0193577 | A1 | 8/2007 | Keller et al. | |
| 2009/0110679 | A1 | 4/2009 | Li et al. | |
| 2010/0236550 | A1 * | 9/2010 | Zeng | A61K 9/0075 128/203.15 |
| 2012/0058049 | A1 * | 3/2012 | Elmaleh | A61K 31/352 424/1.89 |
| 2012/0118991 | A1 | 5/2012 | Keller et al. | |
| 2015/0283113 | A1 * | 10/2015 | Elmaleh | A61K 45/06 424/1.89 |

FOREIGN PATENT DOCUMENTS

| | | |
|---|---|---|
| CN | 101754746 A | 6/2010 |
| CN | 101848733 A | 9/2010 |
| JP | 2001-151673 A | 6/2001 |
| WO | WO 9834596 | 8/1998 |
| WO | WO 2009/010770 A2 | 1/2009 |
| WO | WO 2011/136754 | 11/2011 |

OTHER PUBLICATIONS

Guo et al., "Comparison of Delivery Characteristics from a Combination Metered-Dose Inhaler Using the Andersen Cascade Impactor and the Next Generation Pharmaceutical Impactor," Journal of Pharmaceutical Sciences, vol. 97, No. 8, Aug. 2008, pp. 3321-3334.*
International Search Report application No. PCT/US14/39118 dated Sep. 18, 2014.
Office Action corresponding Australian application No. 2014284656 dated Nov. 3, 2016.
Mitchell et al. "Aerodynamic Particle Size Analysis of Aerosols from Pressurized Metered-Dose Inhalers: Comparison of Andersen 8-Stage Cascade Impactor, Next Generation Pharmaceutical Impactor, and Model 3321 Aerodynamic Particle Sizer Aerosol Spectrometer", AAPS PharmSciTech, 2003, vol. 4, No. 4, Article 54, URL:http://www.aapspharmscitech.org.
Kwong et al. "Comparison of Nebulized Particle Size Distribution with Malvern Laser Diffraction Analyzer Versus Andersen Cascade Impactor and Low-Flow Marple Personal Cascade Impactor", Journal of Aerosol Medicine, 2000, vol. 13, No. 4, pp. 303-314.
Basek, P. et al. "Efficacy of an Isotonic Small Droplet Size Nebulized DSCG on Asthma Control in Children", Acta Paediatrica, 2010, vol. 99, Suppl. 462, p. 115, pp. 155.
Byron, P. R. et al. "Selection and Validation of Cascade Impactor Test Methods", Respiratory Drug Delivery IX, 2004, vol. 1, pp. 169-178. URL: http://www.rddonline.com/education/online_presentations/rddix/rddixbyron/data/downloads/rdd9forum.pdf.
Newman et al. "therapeutic aerosols 1—Physical and practical considerations" Thorax, Jan. 1, 1983 pp. 881-886.
European Search report application No. 14819448.3 dated Feb. 9, 2017.
Office Action corresponding JP application No. 2016-515079 dated May 16, 2017.
Office Action corresponding CN application No. 201480029711.X dated Nov. 4, 2016.
Office Action corresponding CN application No. 201480029711.X dated May 2, 2017.

* cited by examiner

*Primary Examiner* — Aradhana Sasan
(74) *Attorney, Agent, or Firm* — Pearl Cohen Zedek Latzer Baratz LLP

(57) ABSTRACT

Methods of delivering cromolyn to a patient in need thereof, methods of treating amyloid-associated conditions and inflammatory or allergic lung diseases, and blister packs and kits comprising cromolyn are described.

18 Claims, No Drawings

METHODS FOR DELIVERING CROMOLYN

CROSS-REFERENCE TO RELATED APPLICATIONS

This application is a National Phase Application of PCT International Application No. PCT/US2014/039118, filed on May 22, 2014, which claims priority to and the benefit of U.S. Provisional Application Ser. No. 61/826,798, filed May 23, 2013, both of which are incorporated by reference herein in their entirety

FIELD OF THE INVENTION

The invention relates generally to methods of delivering cromolyn to a patient in need thereof, to methods of treating amyloid-associated conditions and inflammatory or allergic lung diseases, and to blister packs and kits comprising cromolyn.

BACKGROUND

Cromolyn (also known as cromoglicic acid, cromoglycate, or cromoglicate) has been approved previously for use in asthma. Its approved form is available as a disodium salt form, cromolyn sodium (also known as disodium cromoglycate or DSCG). Cromolyn demonstrates poor oral absorption. Delivery of cromolyn via inhalation has proven inefficient and difficult due, at least in part, to the hygroscopic nature of cromolyn sodium. For example, micronized powders containing cromolyn sodium particles spontaneously absorb water, forming clumps that impair efficient delivery of the cromolyn powder. See Keller et al. Expert Opin. Drug Deliv. 8, 1-17 (2011) Additionally, the performance and the efficiency of previously used inhalers are highly dependent upon a patient's inspiratory flow rate, leading to a wide variability in the amount of cromolyn sodium that is delivered to a patient. See Richards et al., Journal of Pharmacology and Experimental Therapeutics, 241, 1028-1032 (1987), The present invention provides improved methods and compositions for delivering cromolyn via inhalation, efficiently and consistently over a range of inspiratory flow rates.

SUMMARY OF THE INVENTION

The invention is directed to a method of delivering cromolyn to a patient in need thereof. Such patients include patients in need of systemic delivery of cromolyn, e.g., to the brain or other non-lung tissues. In exemplary embodiments, the patient has an amyloid-associated condition. Patients in need of cromolyn also include patients in need of pulmonary delivery of cromolyn, for lung or airway related conditions. In exemplary embodiments, the patient has an inflammatory or allergic lung disease, such as asthma.

The method comprises administering to the patient via oral inhalation a pharmaceutically acceptable salt or ester of cromolyn in the form of a powder comprising particles of the pharmaceutically acceptable salt or ester of cromolyn. The particles have a mass median aerodynamic diameter (MMAD) of about 1 to about 4 microns. The powder is administered using a device that deposits (a) at least 1.5 mg and (b) at least 30% by weight of the administered amount of pharmaceutically acceptable salt or ester of cromolyn to Stage 4 and higher of a Next Generation Pharmaceutical Impactor (NGI) cascade impactor device at a flow rate of 30 L/min for about 4 seconds.

In related methods, the invention also provides a method of delivering cromolyn to a patient in need thereof, comprising administering to the patient via oral inhalation a pharmaceutically acceptable salt or ester of cromolyn in the form of a powder, under conditions such that (a) at least 1.5 mg and (b) at least 30% by weight of the administered amount of the pharmaceutically acceptable salt or ester of cromolyn is delivered to the lower airways of the patient. As used herein, the term "lower airways" refers to the region of the airways/lung that corresponds to Stage 4 and higher of a Next Generation Pharmaceutical Impactor (NGI) cascade impactor device.

The invention also provides a method of delivering cromolyn to a patient in need thereof, comprising administering to the patient via oral inhalation a pharmaceutically acceptable salt or ester of cromolyn in the form of a powder comprising particles of the pharmaceutically acceptable salt or ester of cromolyn using a dry powder inhaler (DPI) device comprising a chamber comprising a piezoelectric vibrator or an ultrasonic vibrator for deaggregating a powder and an air flow passageway in which the deaggregated powder is picked up and carried for oral inhalation by a patient. The particles of the pharmaceutically acceptable salt or ester of cromolyn have a mass median aerodynamic diameter (MMAD) of about 1 to about 4 microns.

In various embodiments, about 3 mg to about 16 mg (e.g., about 3 mg to about 8 mg) of the pharmaceutically acceptable salt or ester of cromolyn is administered to the patient. Optionally the pharmaceutically acceptable salt or ester of cromolyn is administered with one or more pharmaceutically acceptable excipients. In various embodiments, the powder comprises about 0.1% to about 80%, for example, about 40% to about 80% by weight of an excipient. In various embodiments, the excipient is a monosaccharide, a disaccharide, an oligosaccharide, a polysaccharide, or a polyalcohol, such as lactose, mannitol, or sorbitol.

Additionally, the invention provides a method of treating an amyloid-associated condition in a patient in need thereof. The method comprises administering to the patient via oral inhalation an amount of powder comprising particles of a pharmaceutically acceptable salt or ester of cromolyn via pulmonary delivery, the particles having a mass median aerodynamic diameter (MMAD) of about 1 to about 4 microns, using a device that deposits (a) at least 1.5 mg and (b) at least 30% by weight of the administered amount of pharmaceutically acceptable salt or ester of cromolyn to Stage 4 and higher of a Next Generation Pharmaceutical Impactor (NGI) cascade impactor device at a flow rate of 30 L/min for about 4 seconds.

The invention further provides a method of treating inflammatory or allergic lung diseases in a patient in need thereof. The method comprises administering to the patient via oral inhalation an amount of powder comprising particles of a pharmaceutically acceptable salt or ester of cromolyn, the particles optionally having a mass median aerodynamic diameter (MMAD) of about 1 to about 4 microns, at a frequency of 1 or 2 times daily, each dose comprising about 3 mg to about 16 mg of a pharmaceutically acceptable salt or ester of cromolyn. The dose and/or frequency of delivery according to such methods are reduced compared to the conventional dosages and frequencies.

In various aspects of the invention, the powder comprising particles of a pharmaceutically acceptable salt or ester of cromolyn is administered to a patient using an active dry powder inhaler, such as a dry powder inhaler comprising a chamber comprising a piezoelectric vibrator or an ultrasonic vibrator for deaggregating a dry powder and an air flow passageway in which the deaggregated powder is picked up and carried for oral inhalation by a patient.

In various aspects, the invention is directed to a method for treating an amyloid-associated condition in a patient in need thereof, comprising administering to the patient via oral inhalation an amount of liquid particles of a solution comprising a pharmaceutically acceptable salt or ester of cromolyn using a nebulizer. The particles have a mass median aerodynamic diameter (MMAD) of about 1 to about 4 microns.

The invention further includes use of a pharmaceutically acceptable salt or ester of cromolyn in the preparation of a medicament for treating inflammatory or allergic lung diseases in a patient in need thereof in an amount from about 3 mg to about 16 mg. The medicament is administered via oral inhalation at a frequency of 1 or 2 times daily, and the pharmaceutically acceptable salt or ester of cromolyn is in the form of a powder comprising particles of pharmaceutically acceptable salt or ester of cromolyn optionally having a mass median aerodynamic diameter (MMAD) of about 1 to about 4 microns. The invention further contemplates use of a pharmaceutically acceptable salt or ester of cromolyn in the preparation of a medicament for treating an amyloid-associated condition in a patient in need thereof. The medicament is administered to the patient via pulmonary delivery or oral inhalation. In various embodiments, the pharmaceutically acceptable salt or ester of cromolyn is in the form of a powder comprising particles of a pharmaceutically acceptable salt or ester of cromolyn having a mass median aerodynamic diameter (MMAD) of about 1 to about 4 microns. The medicament is optionally delivered using a dry powder inhaler device as described herein. Alternatively, the pharmaceutically acceptable salt or ester of cromolyn is in solution and administered using a nebulizer.

Additionally, the invention provides a blister pack for delivering cromolyn to a patient in need thereof. The blister pack comprises blisters containing about 3 mg to about 16 mg (e.g., about 3 mg to about 8 mg) of a pharmaceutically acceptable salt or ester of cromolyn. The invention also is directed to a kit comprising a blister pack as described herein and a dry powder inhaler (DPI) device. In some embodiments, the device is an active dry powder inhaler, such as a dry powder inhaler device comprising a chamber comprising a piezoelectric vibrator for deaggregating a dry powder and an air flow passageway in which the deaggregated powder is picked up and carried for oral inhalation by a patient. In some embodiments, the kit further comprises ibuprofen tablets.

Further aspects of the invention may become apparent to those skilled in the art from a review of the following detailed description, taken in conjunction with the appended claims. While the invention is susceptible of embodiments in various forms, described hereinafter are specific embodiments of the invention with the understanding that the disclosure is illustrative, and is not intended to limit the invention to specific embodiments described herein. The entire document is intended to be related as a unified disclosure, and it should be understood that all combinations of features described herein are contemplated, even if the combination of features are not found together in the same sentence, or paragraph, or section of this document. For example, where embodiments concerning a method of delivering cromolyn are described, embodiments involving methods of therapy, kits, and the like that have the same properties and features are specifically contemplated, and the reverse also is true.

In addition to the foregoing, the invention includes, as an additional aspect, all embodiments of the invention narrower in scope in any way than the variations specifically mentioned above. With respect to aspects of the invention described as a genus, all individual species are individually considered separate aspects or the invention. With respect to elements described as a selection within a range, it should be understood that all discrete subunits within the range are contemplated as an embodiment of the invention. Ranges may be expressed herein as from "about" or "approximately" one particular value and/or to "about" or "approximately" another particular value. When such a range is expressed, another embodiment according to the invention includes from the one particular value and/or to the other particular value. Similarly, when particular values are expressed as approximations, but use of antecedents such as "about," "at least about," or "less than about," it will be understood that the particular value forms another embodiment.

With respect to aspects of the invention described or claimed with "a" or "an," it should be understood that these terms mean "one or more" unless context unambiguously requires a more restricted meaning. The term"or" should be understood to encompass items in the alternative or together, unless context unambiguously requires otherwise. If aspects of the invention are described as "comprising" a feature, embodiments also are contemplated "consisting of" or "consisting essentially of" the feature.

DETAILED DESCRIPTION OF THE INVENTION

The invention provides improved methods and compositions for the efficient and consistent delivery of cromolyn via inhalation. Such methods preferably deliver a consistent amount of drug over a wide range of patient inspiratory flow rates. According to some aspects of the inventive method, a large portion of an administered amount of cromolyn is delivered to regions of the lungs that mediate transport into systemic circulation (the bronchi, bronchioles, and alveoli), e.g. the lower airways. Thus, the inventive method can provide an effective means for delivering cromolyn systemically, i.e., into the blood stream (and, by extension, to other non-lung regions of the body, such as the brain). The enhanced delivery efficiency associated with the inventive method allows administration of lower doses of cromolyn and/or less frequent administration of cromolyn, to achieve a desired biological response in any condition requiring lung delivery or systemic delivery. Advantages include improved therapeutic efficacy at conventional doses, or maintained/improved therapeutic efficacy at lower doses and/or lower frequencies of administration, leading to improved ease of use, higher patient compliance, and improved therapeutic benefit, as well as cost savings associated with using reduced amounts of drug. Additionally, many drug packaging systems containing groups of individual delivery units, such as blister pads, have maximum capacities for a single dose of drug contained within individual delivery units, such as blisters. More efficient delivery of cromolyn also advantageously facilitates the packaging of a therapeutically effective dose of cromolyn in each individual delivery unit. Advantages include delivery of a higher dose per single administration, delivery of uniform doses in a multiple administration regimen (i.e., little variability between doses), and/or use of a single individual delivery unit per administration rather than multiple individual delivery units per administration.

The invention is described in further detail below. Section headings are for convenience of reading and not intended to be limiting per se.

Powder Administration

In one aspect, the invention provides a method of delivering cromolyn to a patient in need thereof. Such patients include patients in need of lung or systemic delivery of cromolyn, and include patients with amyloid-associated conditions as well as patients with an inflammatory or allergic, lung disease such as asthma. In any of the embodiments described herein, cromolyn (also known as cromoglicic acid. cromoglycate, cromoglicate, or 5,5'-(2-hydroxypropane-1,3-diyl)bis(oxy)bis(4-oxo-4H-chromene-2-carboxylic acid)) can be administered as a powder comprising particles of a pharmaceutically acceptable salt or ester of cromolyn.

Pharmaceutically acceptable salts are well known to those skilled in the art and include pharmaceutically acceptable inorganic and organic base addition salts, which may be formed with metals or amines, such as alkali and alkaline earth metals or organic amines. Pharmaceutically acceptable salts of compounds may also be prepared with a pharmaceutically acceptable cation. These salts can be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Suitable pharmaceutically acceptable cations are well known to those skilled in the art and include alkaline, alkaline earth, ammonium and quaternary ammonium cations. Examples of metals used as cations are lithium, sodium, potassium, magnesium, ammonium, calcium, aluminum, or ferric, and the like. Examples of suitable amines include ethylamine, diethylamine, piperazine, isopropylamine, trimethylamine, histidine, N,N'-dibenzylethylenediamine, chloroprocaine, choline, ethanolamine, diethanolamine, dicyclohexylamine, ethylenediamine, N-methylglucamine, and procaine. Suitable esters of cromolyn include, but are not limited to, carboxylate esters of one or both of the carboxylic acids of cromolyn, such as aliphatic esters (e.g., methyl esters, ethyl esters, propyl esters, butyl esters such as t-butyl esters, and pentyl esters), aryl esters (e.g., phenyl esters and benzyl esters), and combinations thereof. In one example, the pharmaceutically acceptable salt of cromolyn is disodium cromoglycate.

The pharmaceutically acceptable salt or ester of cromolyn is administered via inhalation, generally via oral inhalation, however, nasal inhalation or a combination of oral and nasal inhalation can also be used. When systemic delivery is desired, administration via inhalation as described herein delivers cromolyn to the lungs of the patient, depositing the pharmaceutically acceptable salt or ester of cromolyn onto surfaces of the lung that allow absorption into the blood stream (e.g., the bronchi, bronchioles, and alveoli), e.g. the lower airways.

The particles of the cromolyn salt or ester typically have a median particle diameter ($D_{50}$ of less than about 2.5 microns, less than about 2 microns, less than about 1.8 microns, less than about 1.5 microns, less than about 1.2 microns, less than about 1 micron, about 0.1 microns to about 2 microns, about 0.5 microns to about 2 microns, about 0.8 microns to about 2 microns, about 1 micron to about 2 microns, about 1.2 microns to about 2 microns, about 1.5 microns to about 2 microns, and/or about 1.8 microns to about 2 microns. The particles of the cromolyn salt or ester optionally have a $D_{90}$ (i.e., the diameter of 90% of the particles) of less than 4 microns, less than 3.9 microns, less than 3.8 microns, less than 3.7 microns, less than 3.6 microns, about 3 microns to about 4 microns, about 3.2 microns to about 3.8 microns, about 3.4 microns to about 3.6 microns, and/or about 3.5 microns to about 3.6 microns.

The particles of the cromolyn salt or ester have a mass median aerodynamic diameter (MMAD) of about 1 to about 4 microns, about 1 to about 3.5 microns, about 1 to about 3 microns, about 1 to about 2.5 microns, and/or about 1 to about 2 microns. Particles of a desired size are obtained by any method, such as a method known to one of skill in the art, including micronization or milling. As used herein, the term "aerodynamic diameter" refers to the diameter of a sphere of unit density that reaches the same velocity in an air stream as a non-spherical particle of arbitrary density. As used herein, the term "mass median aerodynamic diameter" refers to the aerodynamic diameter at which 50% of the particles by mass are larger and 50% are smaller. Methods of determining aerodynamic diameter are known in the art and described in, e.g., Chow et al., "Particle Engineering for Pulmonary Drug Delivery," Pharm. Res., 24 (3), 411-437 (2007).

The particles of the cromolyn salt or ester typically have a geometric standard deviation (GSD) of about 1.3 to about 2.5, about 1.4 to about 2.4. about 1.5 to about 2.3, about 1.6 to about 2.2. about 1.7 to about 2.1, and/or about 1.8 to about 2. As used herein, the term "geometric standard deviation" refers to the spread of an aerodynamic particle size distribution. GSD typically is calculated as follows: $GSD=(d_{84}/d_{16})^{1/2}$, where $d_{84}$ and $d_{16}$ represent the diameters at which 84% and 16% of the aerosol mass are contained, respectively, in diameters less than these diameters.

The powder optionally comprises one or more pharmaceutically acceptable excipients. Suitable excipients are well tolerated by pulmonary tissue, and include, but are not limited to, monosaccharides, disaccharides, oligosaccharides, polysaccharides, polyalcohols, and combinations thereof. Exemplary excipients include, but are not limited to, lactose, mannitol, sorbitol, and combinations thereof. The pharmaceutically acceptable excipient(s), when present, typically are included in the powder in a total amount or about 0.1 to about 80% by weight about 1% to about 80% by weight, about 5% to about 80% by weight, about 10% to about 80% by weight, about 15% to about 80% by weight, about 20% to about 80% by weight, about 25% to about 80% by weight, about 30% to about 80% by weight, about 35% to about 80% by weight, about 40% to about 80% by weight, about 20 to about 75% by weight, about 20% to about 70% by weight, about 20% to about 65% by weight, about 20% to about 60% by weight, about 25% to about 55% by weight, about 30% to about 50% by weight, about 35% to about 45% by weight, and/or about 40% by weight. The pharmaceutically acceptable excipients can be included in an anhydrous form or as a hydrate, such as a monohydrate or higher-order hydrate. The excipient(s) optionally have a particle size of about 250 microns or less, such as about 10 microns to about 150 microns, although other excipient particle sizes may be used in the context of the invention.

A particular administration regimen for a particular patient will depend on several factors, such as the condition being treated, co-therapies administered, the size of the patient, frequency of administration, etc. In various embodiments, the amount of powder that is administered to a patient comprises about 3 mg to about 16 mg of the pharmaceutically acceptable salt or ester of cromolyn, for example, about 3 mg to about 15 mg, about 3 mg to about 14 mg, about 3 mg to about 13 mg, about 3 mg to about 12 mg, about 3 mg to about 11 mg, about 3 mg to about 10 mg, about 3 mg to about 9 mg, about 3 mg to about 8 mg, about 3 mg to about 7 mg, about 4 mg to about 7 mg, and/or about 5 mg to about 6 mg of the pharmaceutically acceptable salt or ester of cromolyn. The amount of powder is optionally administered as a single dose or administration, which may be inhaled in a single breath or span multiple breaths in the course of the single administration. Optionally, the single dose or administration is administered from a single individual delivery unit, such as a single blister or single capsule. This single dose (single administration) may be administered repeatedly to the patient at any interval over the course of a treatment period. For example, a single dose of pharmaceutically acceptable salt or ester of cromolyn (e.g., about 3 mg to about 16 mg) is administered to a patient once a day, twice a day, or three times a day for a treatment period. Examples of treatment periods include at least 1, 2, 3, 4, 5, 6, or 7 days, or at least 1, 2, 3, or 4 weeks, or at least 1, 2, 3, 4, 5 or 6 months, or a year or more.

Generally, administering the powder involves suspending the powder into a gas (such as air or oxygen), thereby forming an aerosol containing the powder and the gas. Concurrently with, or subsequent to, suspension formation, the powder suspension is inhaled by a patient. Typically, the powder is suspended in a gas stream being inhaled by a patient such that administering comprises suspending the powder into an inhaled gas stream.

Suspending the powder into a gas (such as air or oxygen) may be carried out by any means, including vibration. Vibrating the powder generally aerosolizes at least a portion (i.e., at least about 10%, at least about 30%, at least about 50%, at least about 75%, and/or at least about 90%) of the powder. For example, vibrating the powder generally involves suspending at least a portion of the powder in the gas that is in the immediate vicinity of the powder. Additionally, the powder comprising particles of cromolyn and optional pharmaceutically acceptable excipients) can include aggregates, for example, aggregates between two or more cromolyn particles and/or between cromolyn particles and excipient particles. Without intending to be bound by any particular theory, vibrating the powder deagglomerates particle aggregates, advantageously providing smaller particles that are more readily delivered regions of the lungs allowing transport into the blood stream (e.g., the bronchi, bronchioles, and alveoli), e.g. the lower airways. Optionally, the vibrator is vibrated such that the resulting vibrations generate synthetic jets that aerosolize and/or deaggregate the powder. Methods for forming synthetic jets are described, for example, in U.S. Pat. No. 7,318,434, which is incorporated herein by reference in its entirety. Preferably, administering the powder involves vibrating the powder at high frequency, for example, a frequency of about 10 kHz to about 50 kHz, about 15 kHz to about 40 kHz, and/or about 20 kHz to about 30 kHz.

In various embodiments of the invention, the amount of powder comprising particles of a pharmaceutically acceptable salt or ester of cromolyn is administered using a device that deposits (a) at least 1.5 mg and (b) at least 30% by weight of the administered amount of pharmaceutically acceptable salt or ester of cromolyn to Stage 4 and higher of a Next Generation Pharmaceutical Impactor (NGI) cascade impactor device at a flow rate of 30 L/min for about 4 seconds. In exemplary embodiments, the device deposits (a) at least 1 mg, at least 1.5 mg, at least 1.8 mg, at least 2 mg, at least 2.2 mg, at least 2.5 mg, at least 2.8 mg, at least 3 mg, at least 3.2 mg, at least 3.5 mg, at least 3.8 mg, at least 4 mg, at least 4.2 mg, at least 4.5 mg, at least 4.8 mg, at least 5 mg, at least 5.2 mg at least 5.5 mg, about 1.3 mg to about 3.5 mg, about 1.5 mg to about 3 mg, about 1.5 mg to about 5 mg, about 1.5 mg to about 7 mg, about 1 mg to about 3 mg, about 1 mg to about 5 mg, about 1 mg to about 7 mg, about 1.8 mg to about 2.8 mg, about 1.5 mg to about 2.5 mg, and/or about 2 mg to about 2.5 mg and (b) at least 30%, at least 35%, at least 40%, at least 45%, about 30% to about 75%, about 30% to about 65%, about 30% to about 60%, about 30% to about 55%, and/or about 30% to about 50% by weight of the administered amount of pharmaceutically acceptable salt or ester of cromolyn to Stage 4 and higher of an NGI cascade impactor device at a flow rate of 30 L/min for about 4 seconds (or less). As used herein, the term "administered amount" in the phrase "% by weight of the administered amount" refers to the amount of pharmaceutically acceptable salt or ester of cromolyn present in the individual delivery unit (e.g., blister or capsule or other unit dose container) connected to the device. Thus, in one illustrative embodiment, the device delivers at least about 1.8 mg of cromolyn salt or ester to Stage 4 and higher of an NGI cascade impactor as described herein from a blister comprising 6 mg of cromolyn salt or ester (the "administered amount") with or without added excipients. NGI cascade impactors are useful for studying aerodynamic size distribution of aerosols and simulating delivery to different regions of the lung. The respiratory tract forms a particle size-selective system wherein progressively finer particles pass through mouth, larynx and larger airways to be deposited in the peripheral lung (e.g., the alveolar spaces). Similarly, cascade impactors include several "stages" allowing passage of progressively finer particles through the system. An aerosol stream carrying particles passes through each stage at a constant air flow (e.g., 30 L/min). Particles of similar aerodynamic size deposit at a particular stage; smaller particles are deposited at further stages of the NGI cascade impactor than larger particles. At a flow rate of 30 L/min for about 4 seconds of total actuation, Stages 4 and higher of the NGI cascade impactor trap particles having a mass median aerodynamic diameter (MMAD) of about 4 microns or less. The NGI cascade impactor is generally operated under conditions of low relative humidity, such as 20% relative humidity or less. Deposition in the central (bronchial) region of the lung generally peaks with particles having an MMAD of about 4 to about 6 microns, and deposition in the peripheral (alveolar) region of the lung generally peaks with particles having an MMAD of about 2 to about 4 microns. See Mitchell and Nagel, "Particle Size Analysis of Aerosols from Medicinal Inhalers," KONA, 22, 32-65 (2004). Thus, Stages 4 and higher of the NGI cascade impactor at a flow rate of 30 L/min for about 4 seconds of total actuation simulate the regions of the lung providing significant systemic absorption of a medicament into the bloodstream. NGI cascade impactor devices are available from MSP Corporation, Shoreview, Minn.

Advantageously, the inventive methods for delivering cromolyn allow consistent delivery of the active agent over a wide range of flow rates. For example, a consistent amount of powder is delivered to a patient over an inhalation flow rate of 20 L/min to 100 or 20 to 80 L/min, or 20 to 60 L/min. By "consistent amount" is meant a relative standard deviation (RSD) of 10% or less (e.g., 5% or less, 3% or less and/or 2.5% or less) in the amount powder that is received by the patient.

Devices for Powder Administration

The devices for administering the powder described herein include, but are not limited to, a dry powder inhaler (DPI) device, a metered dose inhaler (MDI) device, and a dry powder nebulizer (DPN) device. Suitable devices typically administer a metered dose or a predetermined dose. Such doses generally are administered over a set period of time or a set volume of air. In various embodiments, the device functions independent of the patient's inspiratory flow rate. Thus, for example, the device delivers a consistent amount of cromolyn over a wide range of flow rates, such as an inhalation flow rate of 20 L/min to 100 L/min. or 20 to 80 L/min, or 20 to 60 L/min.

Optionally, the device is a dry powder inhaler comprising a chamber in fluid communication with an air flow passageway. Included in the chamber is a vibrator, e.g., a piezoelectric vibrator or an ultrasonic vibrator, suitable for aerosolizing and/or deaggregating a dry powder. The inhaler optionally includes a lever for activating the piezoelectric or ultrasonic vibrator and for cooperating with a means for puncturing a blister or opening means for opening a blister.

In one embodiment, powder is delivered from the inhaler by receiving a blister containing the powder in an operating position proximal to the piezoelectric or ultrasonic vibrator. The patient places the mouthpiece of the inhaler into the mouth, forms a seal with his/her lips around the mouthpiece, and withdraws air through the air flow passageway while pressing the lever. Upon activation by the lever or other triggering event, the blister is broken, the piezoelectric or ultrasonic vibrator is activated, and the deaggregated powder is picked up into the inspiratory air flow of the patient and carried through the air flow passageway for inhalation by the patient.

The inhaler optionally includes an inhalation flow rate detector which detects the movement of air through the air flow passageway. In some embodiments, when the inhaler includes an inhalation flow rate detector, the event that triggers release of the powder includes movement of air through the air flow passageway above a threshold rate.

The powder is typically delivered in a period of time of about one second to about five seconds of total inhalation time, for example, about one second to about two seconds. The inhalation period can be monitored using a visual indicator, e.g., flashing or changing the color of a light emitting diode, or an audible indicator.

Optionally, the lever, inhalation flow rate, and piezoelectric or ultrasonic vibrator functions are monitored and recorded in memory, such as a flash drive or other computer memory in direct contact with the inhaler or removed from the inhaler but in signal communication with the inhaler. For example, the functional parameters of the device may be transmitted from the device to a remote location, recorded in memory, and made available to healthcare providers via a wired or wireless communication network. The information also optionally may be delivered to point of care devices for monitoring treatment. The recorded performance information allows health care practitioners to monitor the use of the device, which can be particularly beneficial when a patient's ability to operate the device diminishes due to declining cognitive and/or physical health.

Devices also are described in U.S. Pat. Nos. 6,026,809, 7,318,434, 7,334,577, 7,779,837, 8,322,338, and 8,371,294, U.S. Patent Application Publication Nos. 2009/0090361, 2010/0294278, 2012/0077786, International Application Publication No. WO 2005/076872, and European Patent No. 0591136 B1, which are incorporated by reference in their entireties.

Solution Administration Using a Nebulizer

In various embodiments, the invention also includes a method comprising administering cromolyn to a patient using a nebulizer, preferably in a method for treating an amyloid-associated condition in a patient in need thereof. The method comprises administering liquid particles of a solution comprising a pharmaceutically acceptable salt or ester of cromolyn using a nebulizer via inhalation (e.g., oral inhalation) by the patient. These solution particles are droplets of solution in which the pharmaceutically acceptable salt or ester of cromolyn and any optional excipients are dissolved, The pharmaceutically acceptable salt or ester of cromolyn typically is present in the solution at a concentration of about 1 mg/mL to about 100 mg/mL, for example, about 5 mg/mL to about 50 mg/mL, and/or about 10 mg/mL to 20 mg/mL. When included, excipient(s) typically are present in the solution at a concentration of about 1 mg/mL to about 100 mg/mL, for example, about 5 mg/mL to about 50 mg/mL, and/or about 10 mg/ml to 20 mg/mL. The solution particles (i.e., droplets) have a mass median aerodynamic diameter (MMAD) of about 1 micron to about 4 microns, for example, about 1 micron to about 3.5 microns, about 1 micron to about 3 microns, about 1 micron to about 2.5 microns, about 1 micron to about 2 microns, about 2 microns to about 4 microns, and/or about 2.5 microns to about 3.5 microns. The solution particles (i.e., droplets) also optionally comprise a median diameter of less than about 2 microns, less than about 1.8 microns, less than about 1.5 microns, less than about 1.2 microns, less than about 1 micron, about 0.5 microns to about 2 microns, about 0.8 microns to about 2 microns, about 1 micron to about 2 microns, about 1.2 microns to about 2 microns, about 1.5 microns to about 2 microns, and/or about 1.8 microns to about 2 microns. Excipients, dosage, target regions of the lung, delivery amounts and efficiencies, and methods of estimating delivery to target regions of the lung are described above.

Suitable devices for administering cromolyn as a solution include, but are not limited to, a jet, ultrasonic or electronic nebulizers. Such nebulizer devices form aerosolized particles of cromolyn (e.g., a pharmaceutically acceptable salt or ester of cromolyn, such as cromolyn sodium) from a pharmaceutically acceptable solution (e.g., a hypotonic or isotonic solution). The nebulizer device optionally includes a liquid reservoir separated from a mouthpiece or face mask by a vibrating mesh, a piezoelectric element, or a compressed gas atomizer element. In such arrangements, a solution comprising a pharmaceutically acceptable salt or ester of cromolyn is present in the liquid reservoir, and the device produces a mist of particles for oral inhalation. When using a nebulizer, the cromolyn solution is optionally delivered to the patient via inhalation (oral, nasal, or a combination thereof) over the course of about ten minutes or less (e.g., two minutes).

The nebulizer may have any of the features of dry powder administration devices described herein. In exemplary embodiments, the device deposits/delivers at least 1 mg, at least 1.5 mg, at least 1.8 mg, at least 2 mg, at least 2.2 mg, at least 2.5 mg, at least 2.8 mg, at least 3 mg, at least 3.2 mg, at least 3.5 mg, at least 3.8 mg, at least 4 mg, at least 4.2 mg, at least 4.5 mg, at least 4.8 mg, at least 5 mg, at least 5.2 mg, at least 5.5 mg, about 1.3 mg to about 3.5 mg, about 1.5 mg to about 3 mg, about 1.5 mg to about 5 mg, about 1.5 mg to about 7 mg, about 1 mg to about 3 mg, about 1 mg to about 5 mg, about 1 mg to about 7 mg, about 1.8 mg to about 2.8 mg, about 1.5 mg to about 2.5 mg, and/or about 2 mg to about 2.5 mg of pharmaceutically acceptable salt or ester of cromolyn to Stage 4 and higher of an NGI cascade impactor device at a flow rate of 30 L/min for about 4 seconds (or less). In exemplary embodiments, the device deposits/delivers at least 30%, at least 35%, at least 40%, at least 45%, about 30% to about 75%, about 30% to about 65%, about 30% to about 60%, about 30% to about 55%, and/or about 30% to about 50% by weight of the administered amount of pharmaceutically acceptable salt or ester of cromolyn (as defined above) to Stage 4 and higher of an NGI cascade impactor device at a flow rate of 30 L/min for about 4 seconds.

Nebulizers also are described in U.S. Pat. No. 8,263,645 and U.S. Patent Application Publication Nos. 2007/0193577, 2009/0118249, and 2012/0118991, which are incorporated by reference in their entireties.

Amyloid-Associated Conditions

Any of the methods described herein include a method of treating an amyloid-associated condition in a patient in need thereof. In various example embodiments, the method comprises administering to the patient via inhalation an amount of powder comprising particles of a pharmaceutically acceptable salt or ester of cromolyn as described herein. As described above, in alternative embodiments, the method comprises administering to the patient via inhalation an amount of particles of a solution comprising a pharmaceutically acceptable salt or ester of cromolyn using a nebulizer.

Without wishing to be bound by a particular theory, disodium cromolyn penetrates the blood-brain barrier to bind beta-amyloid peptides and inhibit association of amyloid peptides and/or polymerization into oligomers and higher order aggregates. The inhibition of beta-amyloid association and/or polymerization is believed to arrest amyloid-mediated impairment of neurons and may enhance removal of oligomers and/or aggregates from the brain, thereby slowing, stopping or reducing amyloid accumulation in the brain.

By "amyloid-associated condition" is meant a disease or pathological disorder associated with abnormal amyloid aggregation and/or accumulation. See Eisenberg and Jucker, Cell, 148, 1188-1203 (2012). Amyloid accumulation has been linked to a wide variety of disorders ranging from neurodegenerative disorders to systemic amyloidoses to arthritis. Examples of amyloid-associated conditions include, but are not limited to, Alzheimer's disease (beta amyloid), dementia, diabetes mellitus type 2 (IAPP), Parkinson's disease (alpha-synuclein), idiopathetic myeloma, amyloid polyneuropathy, amyloid cardiomyopathy, systemic senile amyloidosis, transmissible spongiform encephalopathy (e.g., Creutzfeldt-Jakob disease) (PrPSc), Down's syndrome, Huntington's Disease (Huntingtin), medullary carcinoma of the thyroid (calcitonin), atherosclerosis (apolipoprotein), rheumatoid arthritis (serum amyloid A), aortic medial amyloid (Medin), prolactinomas (prolactin), familial amyloid polyneuropathy (FAP) (transthyretin), frontemporal lobar degeneration-tau (Tau), Familial British and Danish dementia (BriPP), hereditary non-neuropathic systemic amyloidosis (lysozyme), dialysis-related amyloidosis (beta 2 microglobulin), Finnish amyloidosis (Gelsolin), atrial amyloidosis (atrial natriuretic factor), transthyretin familial amyloidosis (TTR), hereditary fibrinogen alpha-chain amyloidosis (fibrinogen alpha-chain), motor neuron diseases, lattice corneal dystrophy (keratoepithelin), amyotrophic lateral sclerosis (SODI), and cerebral amyloid angiopathy (beta amyloid, cystatin). See, e.g., Koo et al., PNAS, 96(18), 9989-9990 (1999); Eisenberg and Jucker, supra. Other examples of amyloid-associated conditions include head injuries (traumatic brain injury); amyloid-β plaques have been found in patients within hours following traumatic brain injury. See Johnson et al., Nature Reviews Neuroscience, 11, 361-370 (2010).

As used herein, "treating" and "treatment" refers to any reduction in the severity and/or onset of signs or symptoms associated with an ailment, such as an amyloid-associated condition or an inflammatory or allergic lung disease (described below). Accordingly, "treating" and "treatment" includes therapeutic and prophylactic measures that reduce any of the signs or symptoms. One of ordinary skill in the art will appreciate that any degree of protection from, or amelioration of, an amyloid-associated condition or symptom associated therewith is beneficial to a subject, such as a human patient. For example, a reduction in signs such as detectable amyloid plaques can be beneficial. In another example, an increase in soluble amyloid levels in the cerebrospinal fluid from abnormally low levels to normal, age-appropriate levels can also be beneficial. The quality of life of a patient is improved by reducing to any degree the severity of symptoms in a subject and/or delaying the appearance of symptoms. Accordingly, the method in one aspect is performed as soon as possible after it has been determined that a subject is at risk for an amyloid-associated condition or as soon as possible alter the amyloid-associated condition manifests in the subject. For example, due to the rapid development of amyloidβ plaques in traumatic brain injury patients, prognosis may be improved by initiating treatment as soon as possible after the occurrence of the head injury.

Detection of a risk, onset, or presence of amyloid-associated condition is performed using any of a number techniques. Amyloid deposits can be detected ex vivo using, e.g., fluorescent dyes, circular dichroism, and X-ray diffraction. For example, amyloids in biopsied tissue typically demonstrate green birefringence when stained with Congo red and viewed under a polarizing microscope. Amyloid plaques can be detected in vivo using, e.g., magnetic resonance imaging (MRI) (see, Baltes et al., Methods Mol Biol., 711, 511-33 (2011)) and positron emission tomography (PET) (Kepe et al., Methods Enzymol., 412, 144-60 (2006)). Many of the neurodegenerative diseases referenced herein also are diagnosed by conducting mental status and neuropsychological tests (assessing, e.g., memory and problem solving) and blood tests (e.g., blood tests for Alzheimer's disease biomarker signatures). See Burnham et al., "A blood-based predictor for neocortical Aβ burden in Alzheimer's disease: results from the AIBL study," Molecular Psychiatry (April 2013).

Inflammatory or Allergic Lung Diseases

The invention provides methods of treating inflammatory or allergic lung diseases in a patient in need thereof, comprising administering to the patient via inhalation an amount of powder comprising particles of a pharmaceutically acceptable salt or ester of cromolyn as described herein. The dose and/or frequency of administration according to such methods are reduced compared to the conventional dosages and frequencies.

Inflammatory or allergic lung diseases include asthma, chronic obstructive pulmonary disease (COPD), acute respiratory distress syndrome (ARDS), pulmonary fibrosis, cystic fibrosis. Asthma, for example, is a condition associated with inflammation of airway passages in the lungs and airway hyperresponsiveness (AHR). Asthma also is marked by excess mucus production. Symptoms range from minor (e.g., slight shortness of breath) to severe (wheezing, inability to breath, and/or chest tightness) and vary from person to person. During an asthma attack, the lining of airways swell, thereby constricting the passage and reducing airflow to and from the lungs. Asthma is caused or triggered by, for example, infection allergens, chemical substances and fumes, pollutants, medications, physical exertion, stress, and food additives. Asthma is classified into four general categories: mild intermittent (mild symptoms up to two days/week), mild persistent (symptoms more than twice/week, but not daily, and one or two nighttime episodes/month), moderate persistent (daily symptoms and three or four nighttime symptoms/month), and severe persistent (symptoms throughout most days and frequently at night).

As described herein, "treating" and "treatment" refers to any reduction in the severity and/or onset of symptoms associated with inflammatory or allergic lung diseases (e.g., asthma) and, as such, includes therapeutic and prophylactic measures. For example, treatment may result in a reduced number and/or severity of asthmatic attacks in a patient prone to allergy or airway hyperresponsiveness. The method in one aspect is performed as soon as possible after it has been determined that a subject is at risk for inflammatory or allergic lung diseases (e.g., allergy or airway hyperresponsiveness is diagnosed) or as soon as possible after an inflammatory or allergic lung disease (e.g., asthma) manifests in the subject.

Combination Therapies

The pharmaceutically acceptable salt or ester of cromolyn is optionally administered with one or more additional medicaments. For example for amyloid-associated conditions, additional anti-amyloid agents or anti-inflammatory agents can be administered. For inflammatory or allergic lung diseases, additional anti-asthma agents, or anti-inflammation agents, or other agents that are used to treat airway hyperresponsiveness can be administered.

Additional medicaments may be provided in any dosage form, including solid dosage forms (e.g., tablets, capsules and powders) and liquid dosage forms (e.g., solutions, suspensions, emulsions, syrups and elixirs). The additional medicaments may be administered by any known route of administration, including oral (e.g., ingestion or inhalation), injection (e.g., intravenous, intraarterial, intramuscular, subcutaneous, intradermal, intraarticular, intrathecal, epidural, intracerebral, or intraperitoneal), buccal, rectal, topical, transdermal, intranasal, via the pulmonary route, via inhalation or intraophthalmic. The additional medicaments may be administered concurrently with or sequentially (i.e. before or after) with the pharmaceutically acceptable salt or ester of cromolyn.

Additional medicaments include, for example, Levodopa (Sinemet), anticholinergics, Eldepryl, steroids, antihistamines, long-acting or short-acting beta-agonists, immunomodulators (e.g., Omalizumab), and Theophylline.

In the case of amyloid-associated conditions, the additional medicament can be a cholinesterase inhibitor (e.g., Donepezil (Aricept®), rivastigmine (Exelon®), galantamine (Razadyne®, or Tacrine (Cognex®)), a NMDA receptor antagonist (e.g., memantine (Namenda®)), a gamma secretase inhibitor (e.g., LY451039 (Semagacestat, Eli Lily)), a metal ionophore (e.g., PBT2 (Pram)), a statin, and/or an endocannabinoid (e.g., arachidonoylethanolamine, tetrahydrocannabinol, 2-arachidonoyl glycerol, 2-arachidonyl glyceryl ether, N-arachidonoyl-dopamine, or virodhamine). Examples of non-steroidal anti-inflammatory drugs, include, but are not limited to, ibuprofen, acetylsalicylic acid, diflunisal, salsalate, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, nabumetone, piroxicam, meloxicam, tenoxicam, droxicam, lomoxicam, isoxicam, mefenamic acid, meclofenamic acid, flufenamic acid, tolfenamic acid, celecoxib, licofelone, hyperforin and figwort. Preferably, the non-steroidal anti-inflammatory drug is administered orally (via ingestion or inhalation). The non-steroidal anti-inflammatory drug (e.g., ibuprofen) typically is administered in an amount of about 5 mg to about 80 mg per day, for example, about 5 mg to about 60 mg per day, about 5 mg to about 50 mg per day, about 5 mg to about 40 mg per day, about 5 mg to about 30 mg per day, and/or about 5 mg to about 20 mg per day. The non-steroidal anti-inflammatory drug (e.g., ibuprofen) may be administered 1 to 4 times per day, such as 1 to 2 times per day. For example, ibuprofen may be administered in a once-daily dose of about 5 mg to 20 mg.

Blister Packs and Kits

The invention further provides a group of individual delivery units, for example, a blister pack comprising blisters, containing a pharmaceutically acceptable salt or ester of cromolyn. Blister packs are known in the art, and generally comprise a solid support comprising a plurality of spaced bubbles or wells (collectively referred to herein as "blisters") for carrying a predetermined amount of medicament. A film or membrane seals the wells, and is susceptible to puncture or release from the solid support to make the medicament available for delivery. The specific shape, proportions. and dimensions of the blister pack and the individual blisters can be adjusted for use in a particular delivery device. For example, the blister pack is optionally provided as a coil or a circular (e.g., carousel) cartridge for insertion in a dry powder inhaler, and the blisters are shaped as inverted cones or domes. Additionally, the number of blisters (corresponding to the number of doses) may be varied.

The blister pack is composed of a material that protects the contents of the blisters from exposure to the environment and is compatible for use with an inhalation device for delivering cromolyn to a patent. Suitable materials include, but are not limited to, PVC (polyvinyl chloride), PVC/PVDC (polyvinylidene chloride) blends, PE (polyethylene), PP (polypropylene), polystyrene, cellophane, polyester (e.g. a polyester terephthalate), paper, polyamide, PET (polyethylene terephthalate), COC (cyclic olefin copolymer), metallic (e.g., aluminum) foil and any blend thereof. Different materials may be layered to form individual blisters or the blister pack, if desired. Blister packs are further described in, for example, U.S. Pat. Nos. 5,497,763; 7,080,644; 7,828, 150; 7,931,022; and 8,291,900, and International Patent Publication Nos. WO 1999/23180 and WO 1989/01348 (all of which are hereby incorporated by reference in their entirety, and particularly with respect to their respective descriptions of blister packs).

Generally, blisters have a maximum capacity of about 15 to 16 mg of ingredients, which includes both the active ingredient (i.e. cromolyn, or its pharmaceutically acceptable salt or ester) and pharmaceutically acceptable excipients.

In the context of the invention, the blisters of the blister pack contain about 3 mg to about 16 mg of a pharmaceutically acceptable salt or ester of cromolyn, for example, about 3 mg to about 15 mg, about 3 mg to about 14 mg, about 3 mg to about 13 mg, about 3 mg to about 12 mg, about 3 mg to about 11 mg, about 3 mg to about 10 mg, about 3 mg to about 9 mg, about 3 mg to about 8 mg, about 3 mg to about 7 mg, about 4 mg to about 7 mg, about 5 mg to about 7 mg, and/or about 5 mg to about 6 mg of the pharmaceutically acceptable salt or ester of cromolyn.

Optionally, additional amounts of pharmaceutically acceptable excipients are included in the blisters with the cromolyn.

The pharmaceutically acceptable salt or ester of cromolyn is provided in a solid dosage form, preferably a powder containing particles of the pharmaceutically acceptable salt or ester of cromolyn as described herein. The powder optionally comprises one or more pharmaceutically acceptable excipients, as described above. The pharmaceutically acceptable excipients, when present, typically are included in the powder in a total amount of about 0.1% to about 80% by weight, about 1% to about 80% by weight, about 5% to about 80% by weight, about 10% to about 80% by weight, about 15% to about 80% by weight, about 20% to about 80% by weight, about 25% to about 80% by weight, about 30% to about 80% by weight, about 35% to about 80% by weight, about 40% to about 80% by weight, about 20 to about 75% by weight, about 20% to about 70% by weight, about 20% to about 65% by weight, about 20% to about 60% by weight, about 25% to about 55% by weight, about 30% to about 50% by weight, about 35% to about 45% by weight, and/or about 40% by weight.

Alternatively, in some embodiments herein, the cromolyn is provided in liquid solution form.

The invention further provides a kit comprising a blister pack, such as the blister pack described herein, and a dry powder inhaler (DPI) device. In various embodiments, the device is an active dry powder inhaler device, such as a dry powder inhaler device that comprises a chamber comprising a piezoelectric vibrator for deaggregating a dry powder and an air flow passageway in which the deaggregated powder is picked up and carried for inhalation by a patient. The kit optionally includes one or more additional medicaments, such as a non-steroidal anti-inflammatory drug (e.g., ibuprofen, acetylsalicylic acid, difunisal, salsalate, dexibuprofen, naproxen, fenoprofen, ketoprofen, dexketoprofen, flurbiprofen, oxaprozin, loxoprofen, indomethacin, tolmetin, sulindac, etodolac, ketorolac diclofenac, nabumetone, piroxicam, meloxicam, tenoxicam, droxicam, lomoxicam, isoxicam, mefenamic acid, meclofenamic acid, flufenamic acid, tolfenamic acid, celecoxib, licofelone, hyperforin, and figwort). Such additional medicaments may be provided in any known dosage form, including solid dosage forms (e.g., tablets, capsules and powders) and liquid dosage forms (e.g., solutions, suspensions, emulsions, syrups and elixirs).

EXAMPLES

Example 1

A Next Generation Pharmaceutical Impactor (NGI) cascade impactor device (MSP Corporation, Shoreview, Minn., US) was used to assess delivery of cromolyn by four different inhaler devices.

Delivery of cromolyn by a single-use passive dry powder inhaler device was assessed. The passive inhaler device included an active particle dispersion mechanism (ACTIVEMESH, Aespira) involving breath-driven beating of a mesh package containing the powder to be delivered.

A blend containing disodium cromoglycate (DSCG) (Cambrex) and Lactohale LH300 lactose (Friesland Foods Domo) was prepared by blending in an Alpine Picoline high shear mixer (module Picomix) (Hosokawa Alpine, Augsburg, Germany) at a speed of 4000 rpm for 3 minutes. The blend contained 80:20 (wt./wt.) DSCG:lactose. Neat DSCG also was tested. The samples (neat cromolyn or cromolyn:lactose blend) were loaded into the passive dry powder inhaler device and tested using an NGI cascade impactor device at a flow rate of approximately 100 L/min for 2.4 seconds.

The results of testing are provided in Table 1. The passive inhaler device delivered only 3% of the initial dose of neat DSCG and only 6% of the initial dose of blended cromolyn to Stage 4 and higher of the NGI cascade impactor device.

TABLE 1

| DSCG:lactose [wt./wt.] | Initial DSCG dose [mg] | Fine Particle Dose <5 μm [μg] (% of initial dose) | Stages 4 to 8 [μg] (% of initial dose) | MMAD [μm] |
| --- | --- | --- | --- | --- |
| 100:0 | 5 | 430 (9%) | 150 (3%) | >4 |
| 80:20 | 4 | 400 (10%) | 240 (6%) | >4 |

Delivery of cromolyn by a PROHALER pre-metered multidose passive dry powder inhaler device (Aptar) was assessed. The PROHALER inhaler was initially expected to more efficiently deliver cromolyn because the device creates rapidly fluctuating airflow/shear and turbulence to deagglomerate the particles emitted from the blister prior to oral inhalation by the patient. The PROHALER inhaler also included breath-triggered opening of a dose and a blister cartridge system.

Two blends containing disodium cromoglycate (DSCG) (Cambrex) and lactose monohydrate (DMV-Fonterra Excipients) (grade: lactohale 200 with 13% of fines) were prepared by blending at a speed of 90 rpm for 60 minutes. The blends differed in the relative amounts of DSCG and lactose, and contained either 50:50 (wt./wt.) DSCG:lactose or 20:80 (wt./wt.) DSCG:lactose. The blends were filled into blisterstrips, which were then assembled into a PROHALER inhaler device and tested using an NGI device at a flow rate of approximately 35 L/min.

The results of testing are provided in Table 2. The emitted dose represents the total quantity of DSCG fired into the impactor. The fine particle fraction is calculated as follows: fine particle fraction=100%*fine particle dose/emitted dose. A fine particle dose with particles less than 3 μm in size corresponds approximately to the amount of cromolyn delivered to Stage 4 and higher of the NGI device. Thus, the PROHALER inhaler device delivered only about 4.4% of the initial dose of blended cromolyn (50:50 blend) and only about 9.6% of the initial dose of blended cromolyn (20:80 blend) to Stage 4 and higher of the NGI cascade impactor device.

TABLE 2

| DSCG:lactose [wt./wt.] | Initial DSCG dose [mg] | Emitted dose [mg] (% of initial dose) | Fine Particle Dose <3 μm [μg] (% of initial dose) | Fine Particle Fraction <3 μm [%] | MMAD [μm] |
| --- | --- | --- | --- | --- | --- |
| 50:50 | 3.9 | 2.4 (61%) | 170 (4.4%) | 8 | 3.9 |
| 20:80 | 1.6 | 1.1 (69%) | 154 (9.6%) | 15 | 3.1 |

In addition, delivery of cromolyn by a TWISTER inhaler device (Aptar) was assessed. The TWISTER inhaler device is a capsule-based dry powder inhaler. Compared to blisters, capsules typically have much higher drug loading capacities.

A blend containing disodium cromoglycate (DSCG) and lactose was prepared. The blend was assembled into a TWISTER inhaler device and tested using an NCH cascade impactor device at a flow rate of approximately 30 L/min.

The results of testing are provided in Table 3. The TWISTER inhaler device delivered only about 24% of the initial dose of blended cromolyn to Stage 4 and higher of the NGI cascade impactor device.

TABLE 3

| DSCG:lactose [wt./wt.] | Initial DSCG dose [mg] | Emitted dose [mg] (% of initial dose) | Fine Particle Dose <3 μm [μg] (% of initial dose) | Fine Particle Fraction <3 μm [%] | MMAD [μm] |
|---|---|---|---|---|---|
| 20:80 | 4.4 | 3.6 (82%) | 1065 (24%) | 29 | >4 |

Delivery of cromolyn by an active dry powder inhaler device also was assessed. The inhaler device included injection molded plastic components, electronics, a battery, and drug filled blisters. The inhaler included a lever arm, upon actuation of which the blister was placed in contact with a piezoelectric vibrator within the device and then pierced by needles. The inhaler also included an airflow sensor which automatically turned on the piezoelectric vibrator after a minimum inspiratory flow rate was exceeded. Activation of the piezoelectric vibrator deaggregated the powder particles and aerosolized them out of the blister and into the inspiratory airstream. The inhaler included visual feedback at the start of dosing and as confirmation of successful completion of dosing, thereby facilitating improved patient compliance. Similar devices have been shown to deliver a consistent amount of a drug at each of the different flow rates tested, ranging from 20 L/min to 60 L/min.

A blend containing disodium cromoglycate (DSCG) (Cambrex) and lactose monohydrate (DFE Pharma) (grade: lactohale LH201) was prepared by blending at a speed of 150 rpm for 15 minutes. The blend contained 60:40 (wt./wt.) DSCG:lactose. Neat DSCG also was tested. The samples (neat cromolyn or cromolyn:lactose blend) were filled into blisters, which were then assembled into the inhaler device and tested using an NGI device at a flow rate of approximately 30 L/min for 2 seconds.

The results of testing are provided in Table 4. The fine particle dose is the amount of cromolyn recovered below a diameter of 5 μm. The fine particle fraction <5 μm is provided as a percentage of the amount of cromolyn recovered from the NGI cascade impactor device (i.e., the delivered dose). The active inhaler device delivered 42% of the initial dose of neat DSCG and 43% of the initial dose of blended cromolyn to Stage 4 and higher of the NGI cascade impactor device. Thus, in contrast to the results provided in Tables 1 to 3, the results for the active dry powder inhaler device demonstrate delivery of over 1.5 mg and over 30% of the administered dose to Stages 4 and higher of the NGI cascade impactor device.

TABLE 4

| DSCG:lactose blend | Initial DSCG dose [mg] | Fine Particle Dose <5 μm [μg] | Fine Particle Fraction <5 μm [% of delivered dose] | Stages 4 to 8 [μg] (% of initial dose) | MMAD [μg] |
|---|---|---|---|---|---|
| 100:0 | 5 | 2321 | 59 | 2098 (42%) | 2.6 |
| 60:40 | 5.8 | 2858 | 55 | 2505 (43%) | 2.8 |

What is claimed is:

1. A method of delivering cromolyn to a patient in need thereof, comprising administering to the patient via oral inhalation about 3 mg to about 16 mg of a pharmaceutically acceptable salt or ester of cromolyn, optionally including one or more pharmaceutically acceptable excipients, in the form of a powder comprising particles of the pharmaceutically acceptable salt or ester of cromolyn, the particles having a mass median aerodynamic diameter (MMAD) of about 1 to about 4 microns, using a device that deposits (a) at least 1.5 mg and (b) at least 30% by weight of the administered amount of pharmaceutically acceptable salt or ester of cromolyn to Stage 4 and higher of a Next Generation Pharmaceutical Impactor (NGI) cascade impactor device at a flow rate of 30 L/min for about 4 seconds.

2. The method of claim 1, wherein the method comprises administering about 3 mg to about 8 mg of the pharmaceutically acceptable salt or ester of cromolyn, optionally including one or more pharmaceutically acceptable excipients.

3. The method of claim 2, wherein the device is selected from the group consisting of a dry powder inhaler (DPI) device, a metered dose inhaler (MDI) device, and a dry powder nebulizer (DPN) device.

4. The method of claim 3, wherein administering comprises suspending the powder into an inhaled gas stream.

5. The method of claim 4, wherein administering comprises vibrating the powder at high frequency.

6. The method of claim 5, wherein the frequency is about 10 kHz to about 50 kHz.

7. The method of claim 3, wherein the device is a dry powder inhaler comprising a chamber comprising a piezoelectric vibrator or an ultrasonic vibrator for deaggregating a dry powder and an air flow passageway in which the deaggregated powder is picked up and carried for oral inhalation by a patient.

8. A method of delivering cromolyn to a patient in need thereof, comprising administering to the patient via oral inhalation about 3 mg to about 16 mg of a pharmaceutically acceptable salt or ester of cromolyn, optionally including one or more pharmaceutically acceptable excipients, in the form of a powder comprising particles of the pharmaceutically acceptable salt or ester of cromolyn, the particles having a mass median aerodynamic diameter (MMAD) of about 1 to about 4 microns, using a dry powder inhaler (DPI) device comprising a chamber comprising a piezoelectric vibrator or an ultrasonic vibrator for deaggregating a powder and an air flow passageway in which the deaggregated powder is picked up and carried for oral inhalation by a patient, wherein said device deposits (a) at least 1.5 mg and (b) at least 30% by weight of the administered amount of pharmaceutically acceptable salt or ester of cromolyn to Stage 4 and higher of a Next Generation Pharmaceutical Impactor (NGI) cascade impactor device at a flow rate of 30 L/min for about 4 seconds.

9. The method of claim 8, wherein the method comprises administering about 3 mg to about 8 mg of the pharmaceutically acceptable salt or ester of cromolyn, optionally including one or more pharmaceutically acceptable excipients.

10. The method of claim 9, wherein the particles have a geometric standard deviation (GSD) of about 1.3 to about 2.5.

11. The method of claim 10, wherein the powder comprises about 0.1% to about 80% by weight of an excipient.

12. The method of claim 11, wherein the powder comprises about 40% to about 80% by weight of an excipient.

13. The method of claim 11, wherein the excipient is selected from the group consisting of a monosaccharide, a disaccharide, an oligosaccharide, a polysaccharide, a polyalcohol, and lactose.

14. The method of claim 8, further comprising administering a non-steroidal anti-inflammatory drug.

15. The method of claim 14, wherein the non-steroidal anti-inflammatory drug is administered orally or via inhalation.

16. The method of claim 14, wherein the non-steroidal anti-inflammatory drug is administered in an amount of about 5 mg to about 80 mg per day.

17. The method of claim 14, wherein the non-steroidal anti-inflammatory drug is ibuprofen.

18. The method of claim 14, wherein the non-steroidal anti-inflammatory drug is ibuprofen administered in a once-daily dose of about 5 mg to 20 mg.

\* \* \* \* \*